United States Patent
Davenport et al.

(10) Patent No.: US 8,460,280 B2
(45) Date of Patent: Jun. 11, 2013

(54) LOCALIZED FLASHLAMP SKIN TREATMENTS

(75) Inventors: Scott A. Davenport, Half Moon Bay, CA (US); Gregory J. R. Spooner, Kensington, CA (US); David A. Gollnick, San Francisco, CA (US); Steven Christensen, Fremont, CA (US)

(73) Assignee: Cutera, Inc., Brisbane, CA (US)

( * ) Notice: Subject to any disclaimer, the term of this patent is extended or adjusted under 35 U.S.C. 154(b) by 1542 days.

(21) Appl. No.: 11/414,441

(22) Filed: Apr. 28, 2006

(65) Prior Publication Data
US 2007/0255265 A1 Nov. 1, 2007

(51) Int. Cl.
*A61B 18/18* (2006.01)

(52) U.S. Cl.
USPC .......... 606/9; 606/2; 606/10; 606/13; 607/88

(58) Field of Classification Search
USPC ............................ 606/2–19, 131; 607/88–94
See application file for complete search history.

(56) References Cited

U.S. PATENT DOCUMENTS

| | | | |
|---|---|---|---|
| 3,693,623 A | 9/1972 | Harte et al. | 128/303.1 |
| 3,834,391 A | 9/1974 | Block | 606/9 |
| 3,982,541 A * | 9/1976 | L'Esperance, Jr. | 606/3 |
| 4,233,493 A | 11/1980 | Nath | 219/354 |
| 4,298,005 A | 11/1981 | Mutzhas | 128/396 |
| 4,539,987 A | 9/1985 | Nath et al. | 128/303.1 |
| 4,608,978 A | 9/1986 | Rohr | 128/303.1 |
| 4,617,926 A * | 10/1986 | Sutton | 606/9 |
| 5,074,861 A | 12/1991 | Schneider et al. | 606/17 |
| 5,217,455 A | 6/1993 | Tan | 606/9 |
| 5,282,842 A | 2/1994 | Changaris | 607/88 |
| 5,312,395 A | 5/1994 | Tan et al. | 606/9 |
| 5,320,618 A | 6/1994 | Gustafsson | 606/9 |
| 5,344,418 A | 9/1994 | Ghaffari | 606/9 |
| 5,344,434 A | 9/1994 | Talmore | 607/88 |
| 5,405,368 A | 4/1995 | Eckhouse | 607/88 |
| 5,486,172 A | 1/1996 | Chess | 606/20 |
| 5,620,478 A | 4/1997 | Eckhouse | 607/88 |
| 5,626,631 A | 5/1997 | Eckhouse | 607/88 |
| 5,643,334 A | 7/1997 | Eckhouse et al. | 607/88 |
| 5,658,323 A | 8/1997 | Miller | 607/89 |
| 5,683,380 A * | 11/1997 | Eckhouse et al. | 606/9 |

(Continued)

FOREIGN PATENT DOCUMENTS

| | | | |
|---|---|---|---|
| CA | 1041610 | 1/1978 | 326/16 |
| FR | 1139096 | 6/1957 | |

(Continued)

OTHER PUBLICATIONS

A.K. Alimov et al., "Light/Therapy Irradiating Unit," *Geliotekhnika*, vol. 27, No. 2, pp. 67-68, (1991).

(Continued)

*Primary Examiner* — Bill Thomson
*Assistant Examiner* — Lynsey Crandall
(74) *Attorney, Agent, or Firm* — Morrison & Foerster LLP (57) ABSTRACT

A flashlamp device having a small diameter waveguide is disclosed for use in localized dermatological applications. A preferred waveguide has a curvilinear wall surface. The waveguide is supported by a plurality of spaced apart thermally-conductive elements in contact with the curvilinear wall surface allowing sufficient cooling of the waveguide while minimizing the amount of high angle light stripped from the waveguide at points of contact with the contact elements.

10 Claims, 5 Drawing Sheets

U.S. PATENT DOCUMENTS

| | | | |
|---|---|---|---|
| 5,720,772 A | 2/1998 | Eckhouse | 607/88 |
| 5,735,844 A | 4/1998 | Anderson et al. | 606/9 |
| 5,755,751 A | 5/1998 | Eckhouse | 607/88 |
| 5,769,844 A | 6/1998 | Ghaffari | 606/16 |
| 5,776,175 A | 7/1998 | Eckhouse et al. | 607/100 |
| 5,828,803 A | 10/1998 | Eckhouse | 385/88 |
| 5,830,208 A | 11/1998 | Muller | 606/9 |
| 5,836,999 A | 11/1998 | Eckhouse et al. | 607/88 |
| 5,849,029 A | 12/1998 | Eckhouse et al. | 607/104 |
| 5,885,273 A | 3/1999 | Eckhouse et al. | 606/9 |
| 5,964,749 A | 10/1999 | Eckhouse et al. | 606/9 |
| 5,968,034 A | 10/1999 | Fullmer et al. | 606/9 |
| 5,989,283 A | 11/1999 | Wilkens | 607/88 |
| 6,059,820 A | 5/2000 | Baronov | 607/89 |
| 6,080,147 A | 6/2000 | Tobinick | 606/9 |
| 6,096,029 A * | 8/2000 | O'Donnell, Jr. | 606/9 |
| 6,159,204 A | 12/2000 | Hibst | 606/10 |
| 6,174,325 B1 | 1/2001 | Eckhouse | 607/88 |
| 6,193,711 B1 | 2/2001 | Connors et al. | 606/12 |
| 6,214,034 B1 | 4/2001 | Azar | 607/89 |
| 6,228,074 B1 | 5/2001 | Almeida | 606/9 |
| 6,273,883 B1 | 8/2001 | Furumoto | 606/9 |
| 6,280,438 B1 | 8/2001 | Eckhouse et al. | 606/9 |
| 6,324,078 B1 | 11/2001 | Naruo et al. | 363/17 |
| 6,383,176 B1 | 5/2002 | Connors et al. | 606/9 |
| 6,508,813 B1 * | 1/2003 | Altshuler | 606/9 |
| 6,511,475 B1 | 1/2003 | Altshuler et al. | 606/9 |
| 6,514,243 B1 | 2/2003 | Eckhouse et al. | 606/9 |
| 6,517,532 B1 | 2/2003 | Altshuler et al. | 606/9 |
| 6,569,155 B1 | 5/2003 | Connors et al. | 606/9 |
| 6,595,986 B2 | 7/2003 | Almeida | 606/9 |
| 6,632,219 B1 | 10/2003 | Baranov et al. | 606/9 |
| 6,897,238 B2 | 5/2005 | Anderson | 514/563 |
| 7,118,563 B2 * | 10/2006 | Weckwerth et al. | 606/9 |
| 7,147,654 B2 * | 12/2006 | Baumgardner et al. | 607/88 |
| 7,291,140 B2 | 11/2007 | MacFarland et al. | 606/9 |
| 2002/0019625 A1 | 2/2002 | Azar | 606/9 |
| 2002/0107509 A1 * | 8/2002 | Neuberger et al. | 606/9 |
| 2002/0173780 A1 * | 11/2002 | Altshuler et al. | 606/9 |
| 2003/0065314 A1 | 4/2003 | Altshuletr et al. | 606/9 |
| 2003/0069567 A1 * | 4/2003 | Eckhouse et al. | 606/9 |
| 2004/0082941 A1 * | 4/2004 | Connors et al. | 606/9 |
| 2004/0147985 A1 | 7/2004 | MacFarland et al. | 607/90 |
| 2004/0147986 A1 * | 7/2004 | Baumgardner et al. | 607/94 |
| 2004/0167500 A1 * | 8/2004 | Weckwerth et al. | 606/9 |
| 2005/0010198 A1 * | 1/2005 | Marchitto et al. | 606/9 |
| 2005/0177141 A1 | 8/2005 | Davenport et al. | 606/9 |
| 2006/0009749 A1 * | 1/2006 | Weckwerth et al. | 606/9 |
| 2006/0052847 A1 | 3/2006 | Davenport et al. | 607/88 |
| 2008/0183162 A1 * | 7/2008 | Altshuler et al. | 606/9 |

FOREIGN PATENT DOCUMENTS

| | | |
|---|---|---|
| FR | 2 639 834 | 6/1990 |
| GB | 2360946 | 10/2001 |
| JP | H2/86565 | 7/1990 |
| JP | H4/53569 | 2/1992 |
| SU | 1130354 | 12/1984 |
| WO | WO 91/15264 | 10/1991 |

OTHER PUBLICATIONS

A.K. Alimov et al., "Universal Therapeutic Irradiator," *Geliotekhnika*, vol. 28, No. 4, pp. 74-76, (1992).

D. Berger, "Simulating Solar UV, Accurate Simulation of Ultraviolet Solar Radiation Helps Speed Sunscreen Development," 4 pages in length. (In existence as of Dec. 2002).

P. Bjerring et al., "Intense Pulsed Light Source for Treatment of Small Melanocytic Nevi and Solar Lentigines," *Journal of Cutaneous Laser Therapy*, vol. 2, pp. 177-181, (2000).

B.L. Diffey, "The Spectral Emissions from Ultraviolet Radiation Lamps Used in Dermatology," *Photodermatology*, vol. 3, pp. 179-185, (1986).

R. Fitzpatrick et al., "Treatment of Leg Veins: A Comparison of Laser Therapy with a Noncoherent, Multiwave Light Source," pp. 238-239. (In existence as of Dec. 31, 2002).

R.W. Gange et al., "Cutaneous Photosensitization by 8/Methoxypsoralen: Order/Dependent Synergism Between Radiation > 380 nm and Broadband UVA," *The Journal of Investigative Dermatology*, vol. 82, No. 6, pp. 594-597, (1984).

F. Jacka et al., "A Lamp for Cancer Phototherapy," *Aust. J. Phys.*, vol. 36, pp. 221-226 (1983).

N. Kollias et al., "Erythema and Melanogenesis Action Spectra in Heavily Pigmented Individuals as Compared to Fair/Skinned Caucasians," *Photodermatol Photoimmunol Photomed*, vol. 12, pp. 183-188, (1996).

J.A. Parrish et al., "Erythema and Melanogenesis Action Spectra of Normal Human Skin," *Photochem. Photobiol.*, vol. 36, pp. 187-191, (1982).

G. Plewig et al. A New Apparatus for the Delivery of High Intensity UVA and UVA+UVB Irradiation, and Some Dermatological Applications, *British Journal of Dermatology*, vol. 98, pp. 15-24, (1978).

Internet Marketing Material, "ReLume™ Revolutionary Technology for Restoration of Lost Pigment," 3 pages in length.

Marketing Material, "Altus CoolGlide® Hair Removal Laser System," 2 pages in length, (2002).

"DC-DC Power Converters," *Wiley Encyclopedia of Electronics Engineering*, Webster (Ed.), John Wiley & Sons, Inc., pp. 53-63, (1999).

Brochure by Palomar EsteLux™, "Pulsed-Light System," website http://www.palmed.com/laser_estelux.html, printed Jul. 15, 2003, 3 pages in length.

Brochure by Lumenis Aesthetic, "VascuLight™ The World's Most Versatile System for Aesthetic Procedures," website http://www.aesthetic.lumenis.com/wt/content/vasculaight, printed Jul. 15, 2003, 2 pages in length.

Brochure by Lumenis, "VASCU*Light*™ ELITE [Versatility and Speed for the Ultimate Aesthetic System]," Copyright 2002, the Lumenis group of companies, 2 pages in length.

Brochure by Lumenis, "VASCU*Light*™ VS [Versatility and Speed for the Ultimate Aesthetic System]," Copyright 2002, the Lumenis group of companies, 2 pages in length.

Brochure by Lumenis, "VASCU*Light*™ SR [Versatility and Speed for the Ultimate Aesthetic System]," Copyright 2002, the Lumenis group of companies, 2 pages in length.

C. Chess et al., "Cool Laser Optics Treatment of Large Telangiectasia of the Lower Extremities," *J. Dermatol. Surg. Oncol.*, vol. 19, pp. 74-80 (1993).

J.S. Dover et al., "Pigmented Guinea Pig Skin Irradiated With Q-Switched Ruby Laser Pulses," *Arch. Dermatol.*, vol. 125, Jan. 1989, pp. 43-49.

"Laser Surgery of Angiomas with Special Reference to Port-Wine Angiomas," *AMA Association*, Jun. 18-22, 1967, 8 pages in length.

T. Ohshiro et al., "The Ruby and Argon Lasers in the Treatment of Naevi," *Annals Academy of Medicine*, vol. 12, No. 2 (Suppl.), Apr. 1983, 8 pages in length.

T. Ohshiro, "Treatment by Ruby Laser Beams in the Field of Dermatology," "*Japan Medical News*," Separate vol. No. 2768, issued on May 14, 1997, 21 pages in length (English translation attached).

H. Ohtsuka et al., "Ru Laser Histological Studies and Clinical Experiences of Ruby Laser Treatment," 9 pages in length (1991) (1st page is an English Abstract).

L.L. Polla et al., "Melanosomes Are a Primary Target of Q-Switched Ruby Laser Irradiation in Guinea Pig Skin," *The Journal of Investigative Dermatology*, vol. 89, No. 3, Sep. 1987, pp. 281-286.

R.M. Adrian, "Treatment of Facial Telangiectasia Using the VersaPulse® Variable Pulse Width Frequency Doubled Neodymium:YAG Laser: A Case Report," 2 pages in length.

\* cited by examiner

LOCALIZED FLASHLAMP SKIN TREATMENTS

FIELD OF THE INVENTION

The present invention relates to systems and methods for localized dermatological treatments using flashlamps.

BACKGROUND OF THE INVENTION

Visible and near-infra-red laser devices have been used for many years to treat vascular and pigmented lesions. Over the last decade, flashlamps delivering controlled, intense broadband visible-to near-infrared light have gained acceptance for use in hair removal and treatment of various cosmetic skin conditions.

Common applications for flashlamp treatments include treatment of individual vascular and pigmented lesions including facial telangiectasias and cherry hemangiomas or solar lentigines. These types of target lesions are typically small or highly localized. Currently-used flashlamp devices typically deliver energy to the tissue through fairly large, rectangular optical apertures (i.e. where the waveguide has maximum transverse dimensions of approximately 10 by 30 mm, with minimum transverse dimensions of approximately 8-12 mm). When a large aperture device is used to treat small or localized lesions, unwanted side-effects can occur such as hypo and hyper pigmentation and crusting in the skin surrounding the lesion. "Postage stamp" side effects are common with standard rectangular aperture flashlamp devices and are a function of both the size and shape of the treatment area. Sometimes in an effort to minimize these side effects a portion of the optical aperture will be masked or blocked to limit energy delivery to only the treatment area. Specifically, masking objects or agents, such as Teflon tape, gauze or other physical barriers are interposed between the light aperture and the skin to produce specific shapes or small areas of exposure. Other procedures for delivering highly localized treatment attempt to limit the treatment area by relying on the selectivity of the target lesion or structure based on optical absorption characteristics, a technique that may not be optimal for treating patients having relatively dark colored skin.

It is desirable to provide an improved flashlamp device that allows treatment of individual lesions without effecting surrounding areas, without rectangular spot profiles and the associated side effects and to simplify localization of the contacting surface to the target area without sacrificing treatment speed, skin cooling ability, or optical efficiency.

DETAILED DESCRIPTION OF THE DRAWINGS

Figure 1:
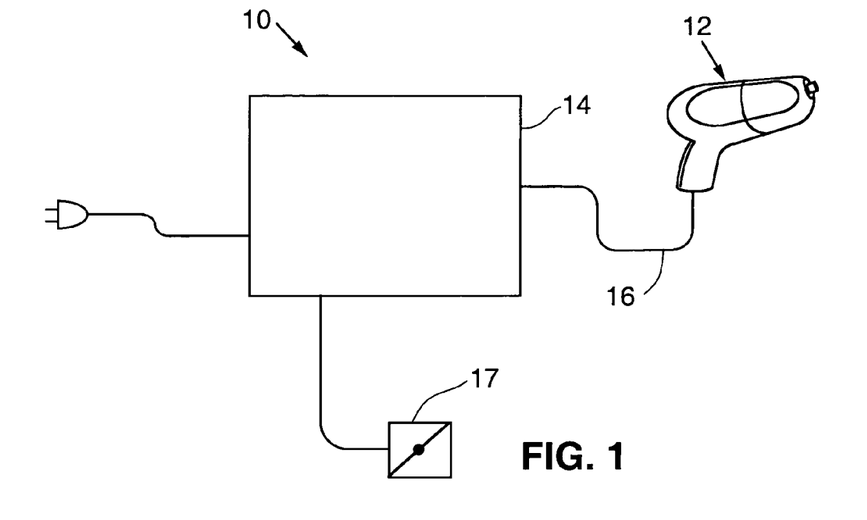
FIG. 1 is a simplified schematic illustration of a dermatological treatment flashlamp system.

FIG. 1 illustrates a dermatological treatment flashlamp assembly 10 that may be used for treating vascular lesions and/or pigmented lesions such as solar lentigines, poikiloderma of Civette, melasma, hyperpigmentation. System 10 includes a handpiece 12 connected to a power and control assembly 14 by a conduit 16. A foot switch 17 is used to initiate delivery of treatment energy from handpiece 12 to tissue.

Figure 2:
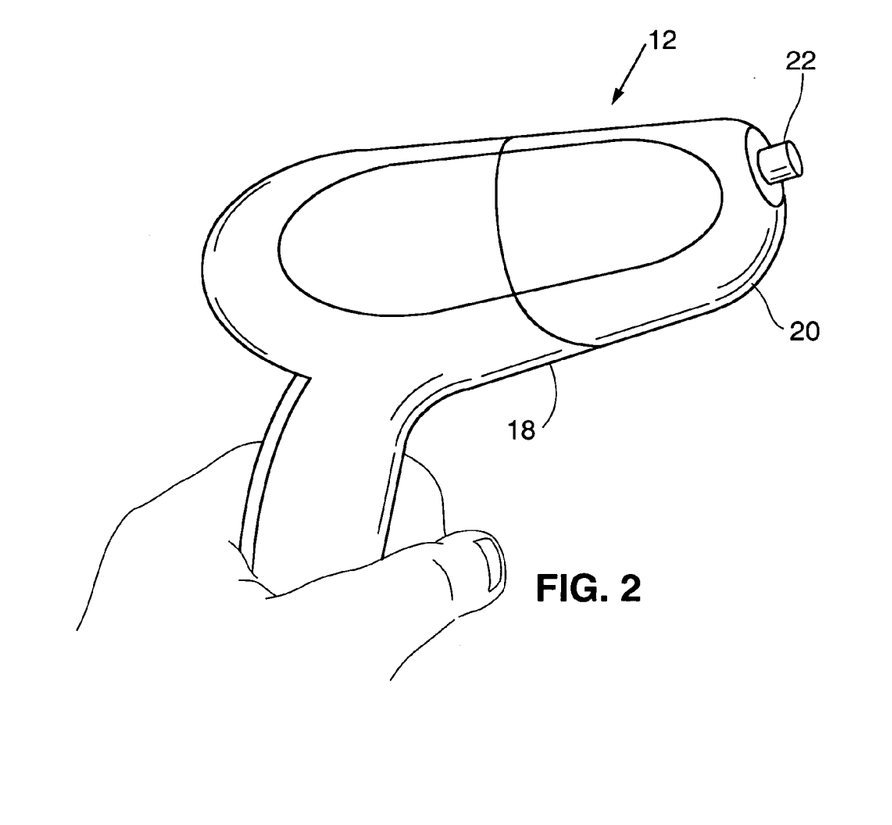
FIG. 2 is a perspective view of a handpiece of the system of FIG. 1.

Handpiece 12, shown in FIG. 2, includes a shell 18 formed of molded plastic pieces enclosing the operational components of the handpiece. Shell 18 includes a tapered nose cone 20. An applicator tip 22 extends from the nosecone 20 and includes a flat distal surface for positioning in contact with skin to be treated.

Figures 3, 4:
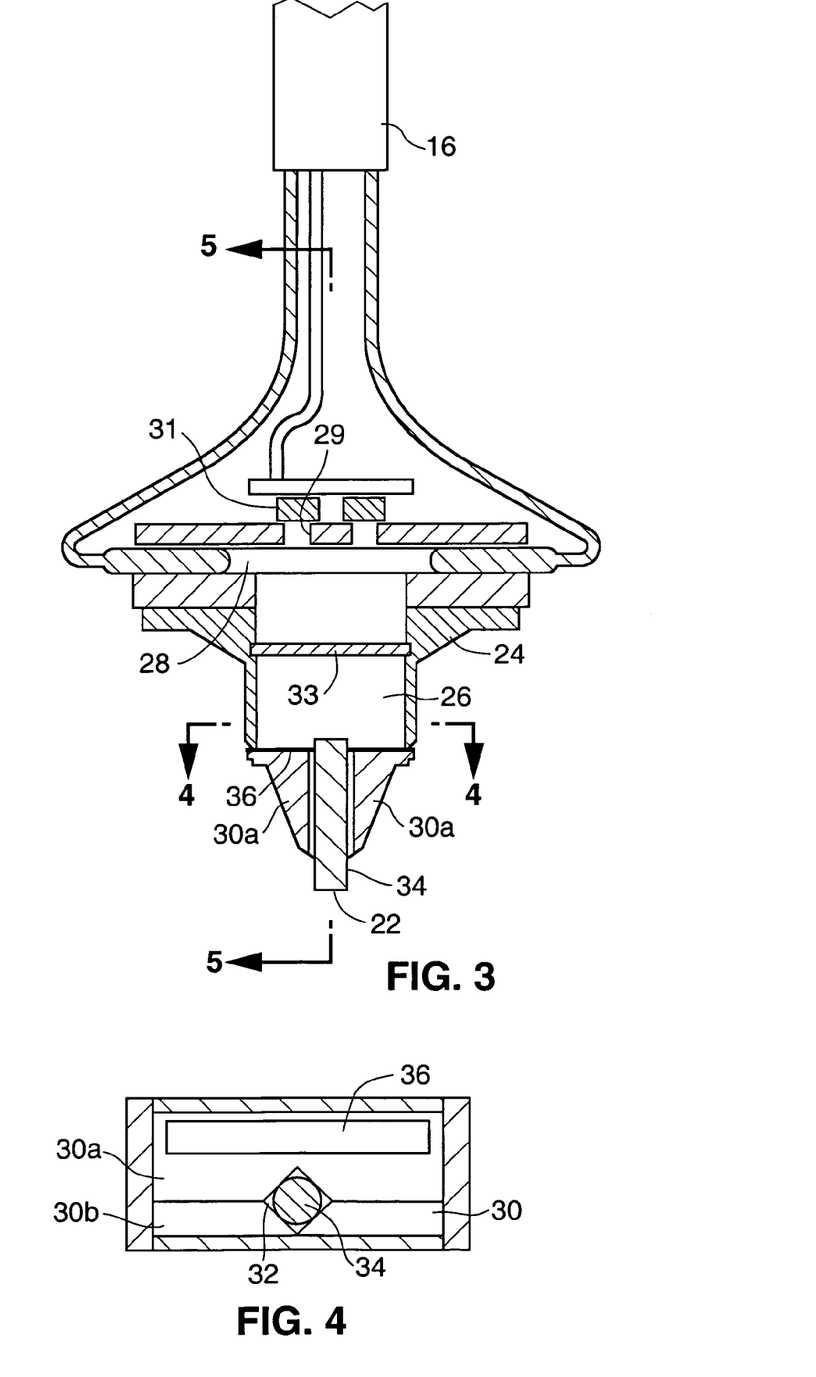
FIG. 3 is a simplified and partially-exploded cross-section view of the operational components of the handpiece of FIG. 2.
FIG. 4 is plan view of the waveguide assembly as viewed from the plane identified as plane 4-4 in FIG. 3.

FIG. 3 shows the handpiece 12 with the shell 18 (FIG. 2) removed. Handpiece includes a reflector housing 24 including a hollow interior 26 having highly reflective interior wall surfaces. In one embodiment, reflector housing 26 is constructed of polished aluminum having interior wall surfaces plated with reflective silver. A transparent protective coating covers the silver. Silver is preferred for its ability to most efficiently reflect light across the range of wavelengths at which optimal treatment benefits are achieved (approximately 500-635 nm). However, in alternative embodiments the interior wall surfaces of the reflective housing may be formed of other materials such as gold or polished aluminum. The reflector housing 24 preferably has interior dimensions of approximately 20-50 mm by 10-15 mm A xenon flashlamp 28 is mounted at one end of housing interior 26 such that energy emitted by the flashlamp is directed into housing interior 26. Fluences in the range of 3-50 J/cm^2 over pulse widths of 1-50 ms are suitable for use with the system 10. One preferred embodiment of a flashlamp 28 can deliver to skin a pulse of light having fluence 3-24 J/cm2 (in a 2-16 ms pulse). The flashlamp is in the form of an elongated tube wherein its length is longer than its diameter.

The glass envelope of the flashlamp may be positioned within a UV-absorbing flowtube which blocks the passage of UV radiation, typically of wavelengths below about 350 nm, by absorbing the UV radiation and converting it to heat. During use, a coolant is circulated through the gap between the flashlamp and the flow tube so as to dissipate the heat. Similar arrangements for circulating coolant through a flow tube are shown and described in US 2004/0147985 and US 2006/0052847, and are found in the Xeo flashlamp handpiece available from Cutera, Inc. of Brisbane, Calif.

The housing 24 includes one or more small apertures 29 adjacent to the flashlamp 28 or to the surrounding flow tube if one is used. One or more photodetectors 31 are positioned adjacent the apertures for sensing the light output transmitted through the flow tube.

An optical filter 33 is positioned within the housing interior 26. Filter 33 is preferably a glass filter that has been coated with a dielectric film, and most preferably one that has been ion beam sputter-coated with tantalum oxide layers. A preferred filter has a transmission band of approximately 500-

635 nm. Wavelengths in this range are strongly absorbed by hemoglobin and melanin and are thus suitable for treating both vascular and pigmented lesions.

Alternative transmission bands may be used if needed for the particular application for which the system will be used. Examples of suitable alternative transmission bands include 560-1200 nm, 600-800 nm, and 540-660 nm.

A pair of clamshell halves 30a, 30b are positioned at the end of the housing interior, opposite from the flashlamp 28 and in contact with the rod 34. These elements are formed of a thermally conductive material, such as copper, to facilitate cooling of the rod 34 as described below. The clamshell halves together define a mounting member for the rod.

In a preferred embodiment, rod 34 is a cylindrical rod formed of barrel polished sapphire. Alternate geometries may instead be used for the rod, particularly those having curvilinear lateral cross-sections (e.g. elliptical). Rods with rectangular lateral cross-sections or other geometries using planar wall surfaces may also be used although non-rectangular cross-sections are preferred.

In use, the rod 34 functions as a waveguide for light emitted by the flashlamp. In a preferred embodiment, rod 34 has a diameter of approximately 6 mm and a length of approximately 1 cm, although diameters in the range of 1-20 mm and lengths in the range of 0.5-5 cm are also suitable. A preferred rod 34 will have a high aspect ratio, i.e. in the range of 3-1 to 10-1, wherein the aspect ratio is defined as the length of the waveguide relative to the diameter of the waveguide. As can be seen in FIG. 3, the longitudinal axis of the rod is oriented perpendicularly to the longitudinal axis of the flashlamp. Further the proximal end of the rod is located within the housing and spaced from the flashlamp. Still further, the reflector 26 is aligned with the flashlamp and positioned between the flashlamp and the rod.

The proximal end of the rod 34 is disposed within the reflector housing interior 26. The distal end of the rod 34 forms the applicator tip 22 (FIG. 2) intended to be placed in contact with tissue during use of the system. The small diameter of the waveguide rod 34 allows the treatment energy to be targeted to a small area, and it allows the user to easily see where on the skin the energy is being delivered (in contrast to a large aperture system in which a small treatment areas is created using a masking object, rendering it more difficult for the user to see the target tissue location). The small contacting area of the tip 22 also facilitates treatment of areas of high curvature or convexity. In preferred embodiments, the surface area of the tip 22 is less than 1.5 cm$^2$, and is most preferably less than 0.8 cm$^2$.

Figure 5:
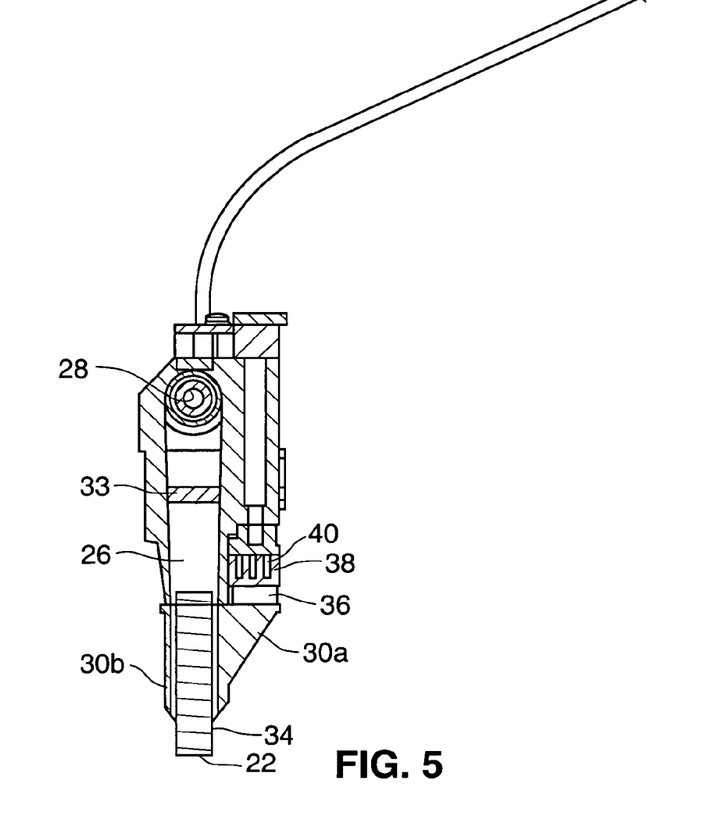
FIG. 5 is a cross-section view taken along the plane designated 5-5 in FIG. 3 but in which the waveguide is shown attached to the reflector housing.

Referring to FIG. 5, the sapphire rod 34 is cooled using a thermoelectric cooler 36 positioned on the thermally conductive clamshell half 30a. A copper cooling block 38 is positioned against the thermoelectric cooler. Cooling fluid is circulated through fluid channels 40 in the cooling block 38 to dissipate heat generated on the wall of the thermoelectric cooler 36. The degree of cooling is determined in part by the particular treatment to be carried out. For example, the cooling requirements of a vascular treatment are greater than the cooling requirements for pigmented lesions. One embodiment of a treatment system may provide the user with the option to select between a "vascular mode" for which the rod 34 will be cooled to a temperature in the range of 5-15° C. (preferably approximately 10° C.), and a "pigmented mode" for which rod will be cooled to a range of 15-25° C. (preferably approximately 20° C.).

Figure 6A:
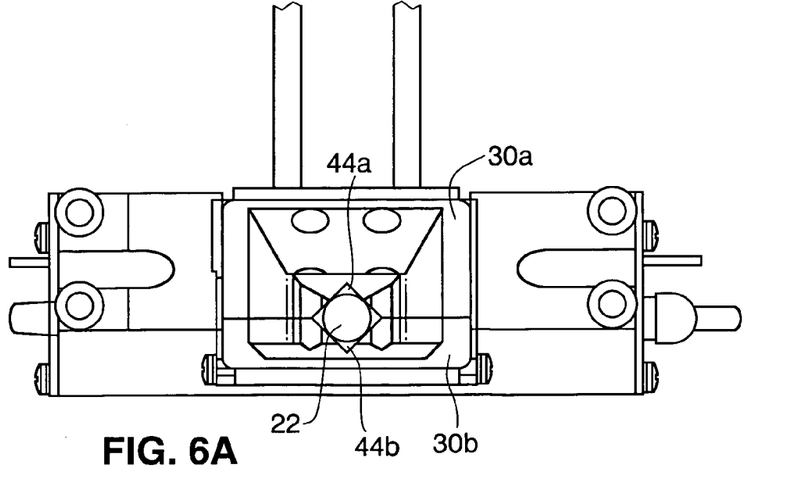
FIG. 6A is a bottom perspective view of the treatment end of the handpiece assembly of FIG. 2.
Figure 6B:
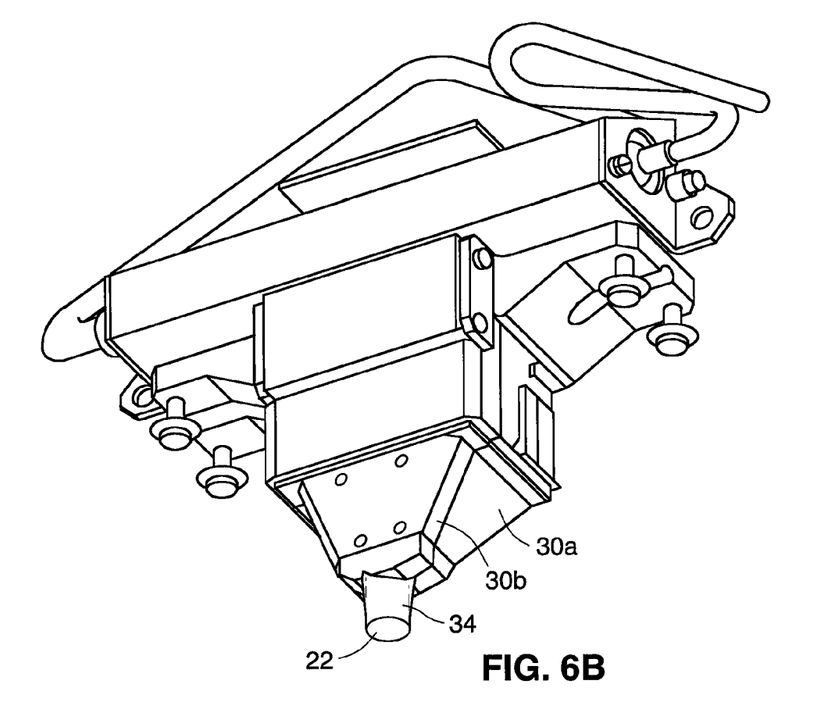
FIG. 6B is a side perspective view of the handpiece assembly of FIG. 6A.

The manner in which the rod 34 is mounted is selected to provide good thermal contact between the thermal-electrically clamshell halves 30a and 30b and the rod so as to adequately cool the skin. However, placing components in contact with the exterior surface of the rod will interfere with the total internal reflection of the waveguide and can lead to significant losses in optical efficiency. The preferred mounting method is best shown in FIGS. 6A and 6B and includes V-grooves 44a, 44b formed in the pair of copper clamshell halves 30a, 30b. V-grooves 44a, b are arranged such that when the halves and sapphire rod 34 are arranged as shown, the interface between rod and V-Grooves 44a, b form four lines of contact parallel to the longitudinal axis of the rod, where each line contact is positioned at the point where the planar wall of a V-grooves contacts the cylindrical surface of the rod. This mounting arrangement for the rod helps to prevent significant loss of light from the waveguide.

Figure 7A:
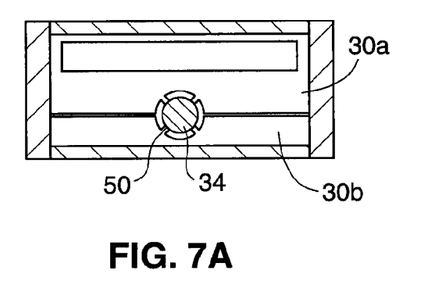
FIGS. 7A and 7B are plan views similar to FIG. 4 showing two alternative mounting arrangements for the waveguide.
Figure 7B:
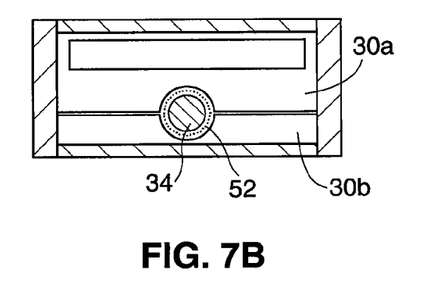

Although the contact features provided by the V-grooves have been found beneficial, the system can incorporate other mounting arrangements that limit the amount of surface contact but allow for reasonable thermal coupling. Mounting arrangements using other types of spaced apart line contact features are particularly suitable. For example, as shown in FIG. 7A, rod 34 may be supported by thermally conductive ribs, or fingers 50 extending into contact with the rod 34 to form line or point contacts with the curvilinear surface of the rod. These ribs or fingers may have planar or curvilinear surfaces contacting the rod 34. Alternatively, as shown in FIG. 7B, a mesh element 52 of thermally conductive material having a minimal surface contact area might be used, such that strands of the mesh are in contact with the rod. Other contact features providing a suitable amount of contact given the rod diameter and length, the temperature to which cooling is desired, and the desired level of optical efficiency may alternatively be used.

Vascular and melanin-containing pigmented lesions of the type to be treated using the system 10 are normally found in the epidermis or upper dermis. The hand piece 12 is preferably designed to facilitate shallow penetration by producing a highly-divergent energy pattern. The advantage to an increased divergence is that relatively high fluences at the skin contacting surface are achievable, while limiting the penetration of the light (by scatter), since the more the light diverges when it impinges on the skin, the less likely the light is to penetrate the skin. Such an approach may be used to treat superficial lesions while leaving deeper structures, such as hair follicles, undamaged. This allows the system 10 to be used to treat pigmented and vascular lesions in areas of the body where hair is present and from which hair removal is not desired. For other applications for which deeper penetration is needed (e.g. treatment of deeper lesions or treatments where hair removal is desired), the lamp size, distance between the lamp and the waveguide, and the size of the waveguide may be selected to produce a less divergent energy pattern.

Figure 8A:
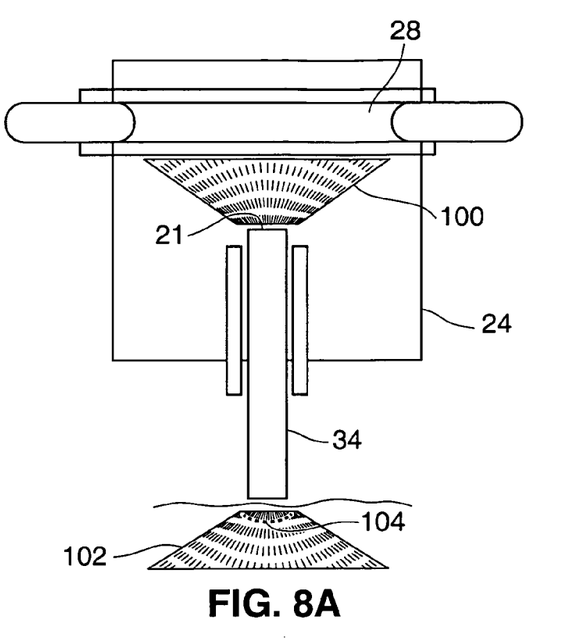
FIG. 8A schematically illustrates the shape of the cone of light entering the waveguide in handpiece of FIG. 2, and further illustrates the corresponding distribution of light energy in the skin.
Figure 8B:
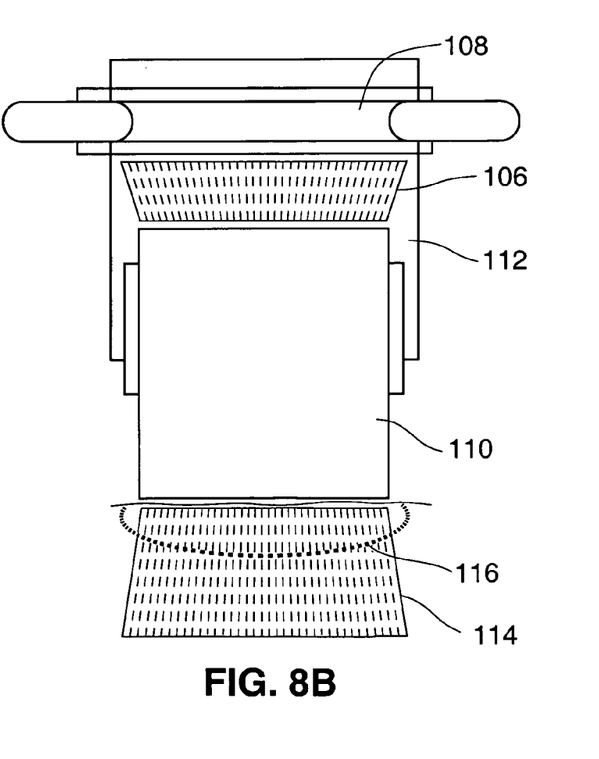
FIG. 8B is a similar drawing illustrating the acceptance cone of light and the light intensity distribution for a prior art system employing a large surface area waveguide.

FIG. 8A schematically illustrates the flash lamp 28, rod 34, and reflector housing 24. As shown, the lateral dimensions of the reflector housing 24 are significantly larger than those of the lateral dimensions of the waveguide rod 34. Preferably, the ratio of the maximum lateral dimension of the reflector housing to the ratio of the maximum lateral dimension of the waveguide is in the range of approximately 3:1 to 9:1. The pattern of light 102 exiting the rod 34 is highly divergent as shown. The depth contour 104 for therapeutic fluences within the skin is thus shallow (i.e. approximately 0.1-1 mm) and allows for use of the system 10 in hairy regions of the body without damaging the underlying hair follicles. By way of contrast, in a conventional dermatological flashlamp illustrated in FIG. 8B, the lateral dimensions of the waveguide 110 and reflector housing 112 are similar. Thus, a less divergent and thus more deeply penetrating energy pattern 114 is produced, giving a deeper depth contour 116 at therapeutic fluences and preventing use of the prior art flashlamp 108 in hairy regions of the body if hair removal is not desired.

A cone of light 100 (FIG. 8A) that illuminates the entrance aperture 21 of the waveguide at the entrance of rod 34 is defined by the solid angle subtended by source 28 as viewed by the entrance aperture 21. Source 28 dimensions and entrance aperture 21 position and lateral dimensions are arranged such that the solid angle that the illumination cone 100 subtends is substantially larger than that in conventional intense pulse light (IPL) devices (see cone 106, FIG. 8B). The result is that the light entering entrance aperture 21 is closer to the acceptance angle of the waveguide (which is defined by the critical angle for total internal reflection of the waveguide material) and is preferably in the range of 25-40°. Since the light guiding in the waveguide has, on average, a higher angle than for a conventional IPL device, spoiling the total internal reflectance angle by contacting the waveguide surface with any material other than air has the potential to "strip", or refract out, the higher angle light. This can adversely affect the amount of fluence available at the skin-contacting surface and the depth contour for therapeutic fluences. Mechanically mounting and thermally contacting the waveguide therefore becomes a challenge. In the embodiments described above, efficiency is maintained using mounting structures that permit only four lines of contact with the cylindrical waveguide, allowing sufficient cooling of the waveguide while minimizing the amount of high angle light stripped from the waveguide at points of contact with the cooling and mounting surfaces.

During use of the system, the user may input one or more parameters, such as the desired optical fluence for each pulse, the period between pulses (which may be the same or different), and the number of pulses delivered each time foot switch 17 is depressed. The user may also input instructions corresponding to the desired degree of cooling. In one embodiment, the user may select between "vascular mode" which preferably provides for cooling to a temperature of approximately 10° C., or "pigmented mode" for which the rod 34 is cooled to a temperature of approximately 20° C.

The lamp is operated at a high current density to shift the output spectrum of the flashlamp to the blue range (corresponding to the absorption range for the target lesions). In a preferred mode of operation, the system maintains a consistent output spectrum over different fluence levels. This may be achieved by maintaining a fixed peak power level while varying the pulse width with the fluence level. In a preferred system, the pulse width increases from 2 ms to 16 ms as the fluence increases from 3 J/cm2 to 24 J/cm2 so as to keep maintain the flash lamp at a constant color temperature. Short duration pulse widths of this nature are also advantageous for treating small facial vessels in that they match or are shorter than the vessel thermal relaxation times (e.g. the thermal relaxation time of a typical 100 micron facial vessel is approximately 10 ms).

The flow of coolant through the handpiece is actuated through the use of user controls. Thermoelectric device 36 cools the rod 34 to the predetermined temperature. The tip 22 of the rod 34 is placed at the target site on the patient's skin, and foot switch 17 is depressed, causing radiation to pass from flashlamp 28 through rod 34. A single pulse or a train of pulse is delivered to the tissue depending on the application. The handpiece 12 may be held in a single location for the duration of treatment, moved over an area of the patient's skin. The thermoelectric device 36 keeps the rod 34 cool and maintains a cool skin temperature while the radiation treats the pigmented or vascular lesion.

Modification and variation can be made to disclosed embodiments without departing from the subject of the invention is defined in the following claims.

Any and all patents, patent applications and printed publications referred to above are incorporated by reference.

We claim:

1. A handpiece for generating radiation to treat tissue comprising:
   a housing having a mounting member located at a delivery end thereof;
   an elongated flashlamp mounted within the housing;
   an elongated, cylindrical optical waveguide having a circular cross section and being formed from sapphire and supported within said mounting member, wherein the longitudinal axis of the waveguide is oriented perpendicularly to the longitudinal axis of the flashlamp, said waveguide having a proximal end located within the housing and spaced from the flashlamp and a distal end projecting beyond the end of the mounting member of the housing;
   an optical reflector mounted within the housing, said optical reflector being aligned with the flashlamp and positioned between the flashlamp and the waveguide, wherein optical radiation emitted from the flashlamp is directed by the optical reflector into the proximal end of the waveguide, wherein said radiation is totally internally reflected within the waveguide and is emitted out of the distal end thereof; and
   a cooling element thermally coupled to the mounting member and wherein the mounting member includes four planar walls oriented so that the planar surfaces thereof abut the cylindrical surface of the waveguide so as to create only line contacts with the outer surface of the waveguide extending parallel to the longitudinal axis along the length thereof so that total internal reflection losses are minimized.

2. A handpiece as recited in claim 1, wherein the ratio of the length of the waveguide along the longitudinal axis thereof to the diameter of the waveguide is in the range of 3:1 to 10:1.

3. A handpiece as recited in claim 1, wherein the width of the optical reflector is less than nine times the width of the waveguide.

4. A handpiece as recited in claim 1, wherein the surface area of the distal end of the waveguide is less than 1.5 cm$^2$.

5. A handpiece as recited in claim 1, wherein the diameter of the waveguide is between 5.5 to 6.5 mm.

6. A handpiece for generating radiation to treat tissue comprising:
   a housing having a mounting member located at a delivery end thereof;
   an elongated flashlamp mounted within the housing;
   an elongated, cylindrical sapphire rod supported within said mounting member, said rod having a circular cross-section, wherein the longitudinal axis of the rod is oriented perpendicularly to the longitudinal axis of the flashlamp, said rod having a proximal end located within the housing and spaced from the flashlamp and a distal end projecting beyond the end of the mounting member of the housing, and with the surface area of the distal end of the rod being less than 1.5 cm$^2$;
   an optical reflector mounted within the housing, said optical reflector being aligned with the flashlamp and positioned between the flashlamp and the rod, wherein optical radiation emitted from the flashlamp is directed by the optical reflector into the proximal end of the rod, wherein said radiation is totally internally reflected within the rod and is emitted out of the distal end thereof; and a cooling element thermally coupled to the mounting member and wherein the mounting member includes four planar walls oriented so that the planar surfaces thereof abut the cylindrical surface of the rod so as to create only line contacts with the outer surface of the rod extending parallel to the longitudinal axis along the length thereof so that total internal reflection losses are minimized.

7. A handpiece as recited in claim 6, wherein the width of the optical reflector is at least three times greater than the diameter of the rod.

8. A handpiece as recited in claim 7 wherein the width of the optical reflector is less than nine times the diameter of the rod.

9. A handpiece as recited in claim 7, wherein the diameter of the rod is between 5.5 to 6.5 mm.

10. A handpiece as recited in claim 6, wherein the ratio of the length of the rod along the longitudinal axis thereof to the diameter of the rod is in the range of 3:1 to 10:1.

* * * * *